(12) United States Patent
Solina et al.

(10) Patent No.: US 11,777,127 B2
(45) Date of Patent: Oct. 3, 2023

(54) MICROBIAL FUEL CELL CATHODE AND METHOD OF MAKING SAME

(71) Applicant: MICRORGANIC TECHNOLOGIES, INC., Castelton-On-Hudson, NY (US)

(72) Inventors: Brent A. Solina, Castelton, NY (US); Alex Carlton, Troy, NY (US)

(73) Assignee: MICROGANIC TECHNOLOGIES, INC., Castleton-On-Hudson, NY (US)

( * ) Notice: Subject to any disclaimer, the term of this patent is extended or adjusted under 35 U.S.C. 154(b) by 498 days.

(21) Appl. No.: 16/612,740

(22) PCT Filed: May 14, 2018

(86) PCT No.: PCT/US2018/032497
§ 371 (c)(1),
(2) Date: Nov. 11, 2019

(87) PCT Pub. No.: WO2018/209336
PCT Pub. Date: Nov. 15, 2018

(65) Prior Publication Data
US 2020/0083553 A1 Mar. 12, 2020

Related U.S. Application Data

(60) Provisional application No. 62/505,530, filed on May 12, 2017.

(51) Int. Cl.
*H01M 8/16* (2006.01)
*C02F 1/461* (2023.01)
(Continued)

(52) U.S. Cl.
CPC ........... *H01M 8/16* (2013.01); *C02F 1/46109* (2013.01); *C02F 3/005* (2013.01); *H01M 4/8626* (2013.01);
(Continued)

(58) Field of Classification Search
CPC ............. H01M 4/8668; H01M 4/8673; H01M 4/8807; H01M 4/8817; H01M 4/9008;
(Continued)

(56) References Cited

U.S. PATENT DOCUMENTS 8,377,149 B2 * 2/2013 Dopp .................. H01M 4/8605
29/25.03
9,837,677 B2 12/2017 Solina
(Continued)

FOREIGN PATENT DOCUMENTS

| EP | 2770565 | 8/2014 |
| GN | 106058269 | 10/2016 |
| KR | 20130038470 A | 4/2013 |

OTHER PUBLICATIONS

Extended European Search Report for Application No. EP 18798711.0, dated Jan. 29, 2021.
(Continued)

*Primary Examiner* — Brittany L Raymond
(74) *Attorney, Agent, or Firm* — HESLIN ROTHENBERG FARLEY & MESITI P.C.

(57) ABSTRACT

Provided is a microbial fuel cell including a cathode and an anode, wherein the cathode includes a waterproof gas diffusion layer including a siloxane and a catalyst layer including a binder, wherein a surface of the gas diffusion layer opposite the catalyst layer contacts air, and the anode includes electrogenic bacteria. Also provided is a method for making a microbial fuel cell, including fabricating a cathode, wherein fabricating includes disposing a siloxane solution onto a surface of a substrate, wherein the siloxane solution includes a siloxane and a solvent, drying the siloxane solution to form a waterproof gas diffusion layer, and placing the gas diffusion layer on a catalyst layer including a binder, and facing an anode with the cathode
(Continued)

whereby the gas diffusion layer faces away from the anode and contacts air.

17 Claims, 4 Drawing Sheets

(51) Int. Cl.
| | |
|---|---|
| *C02F 3/00* | (2023.01) |
| *H01M 4/86* | (2006.01) |
| *H01M 4/88* | (2006.01) |
| *H01M 4/90* | (2006.01) |
| *C02F 103/06* | (2006.01) |
| *C02F 103/28* | (2006.01) |
| *C02F 103/32* | (2006.01) |

(52) U.S. Cl.
CPC ....... *H01M 4/8668* (2013.01); *H01M 4/8673* (2013.01); *H01M 4/8807* (2013.01); *H01M 4/8892* (2013.01); *H01M 4/9083* (2013.01); *C02F 2001/46142* (2013.01); *C02F 2001/46166* (2013.01); *C02F 2103/06* (2013.01); *C02F 2103/28* (2013.01); *C02F 2103/32* (2013.01)

(58) Field of Classification Search
CPC ... H01M 4/9083; H01M 8/16; C02F 1/46109; C02F 3/005; C02F 2001/46142; C02F 2001/46166

See application file for complete search history.

(56) References Cited

U.S. PATENT DOCUMENTS

| | | | |
|---|---|---|---|
| 2003/0203271 A1* | 10/2003 | Morse | H01M 8/1097 |
| | | | 429/442 |
| 2007/0059565 A1* | 3/2007 | Siu | H01M 8/0245 |
| | | | 429/513 |
| 2013/0089807 A1 | 4/2013 | Hong et al. | |
| 2015/0165653 A1 | 6/2015 | Medina et al. | |
| 2015/0349350 A1* | 12/2015 | Liu | H01M 4/8657 |
| | | | 429/2 |
| 2016/0036083 A1 | 2/2016 | Solina | |
| 2018/0097239 A1* | 4/2018 | Kam | H01M 8/02 |
| 2018/0358627 A1* | 12/2018 | Suzuki | H01M 4/8668 |

OTHER PUBLICATIONS

International Search Report and Written Opinion of the International Searching Authority for International Application No. PCT/US2018/032497 dated Sep. 13, 2018.

* cited by examiner

MICROBIAL FUEL CELL CATHODE AND METHOD OF MAKING SAME

CROSS-REFERENCE TO RELATED APPLICATIONS

This application is a national stage filing under 35 U.S.C. § 371 of International Application No. PCT/US2018/032497, filed on May 14, 2018, published as WO 2018209336 on Nov. 15, 2018, and claims benefit of priority from U.S. Provisional Patent Application No. 62/505,530, filed May 12, 2017. The disclosures of each of the said applications are incorporated by reference in their entireties herein.

FIELD OF THE INVENTION

The invention relates to microbial fuel cell cathodes used in the application of microbial fuel cells (MFCs) and having a waterproof gas diffusion layer and methods of making and using same. More particularly, the invention relates to the scalable production of a non-porous siloxane-containing gas diffusion layer that adheres to a catalyst layer and can contain a percentage of carbon filler materials.

BACKGROUND OF THE INVENTION

Microbial fuel cells utilize electrogenic microorganisms to create a potential gradient between electrons in part by taking advantage of exo-electrogenic catabolism of organic compounds. This has been used to reduce organics in municipal and industrial waste streams, to desalinate water, to power underwater sensors and autonomous devices and to generate power from soil. While there is an established understanding of many aspects of microbial fuel cell design and operation, methods of manufacture on a full scale have been lacking.

Within a microbial fuel cell, a biofilm of exo-electrogenic microorganisms may form on the anode and catabolize organics to generate a potential. When coupled with a counter-electrode, a cathode, this potential generates a current flow via delivery of the electrons to the reactive species at the cathode. In microbial fuel cells, this reactive species may be oxygen. The rate of transfer of electrons in a microbial fuel cells may therefore be ultimately governed by the cathode and the relatively slow reduction of oxygen.

While air-breathing cathodes are employed in other electrochemical fields, the usual design approaches have yielded less than optimal performance in the area of microbial fuel cells. Electrodes which require gas transfer into or in close proximity of electrolyte and electrode generally rely on a material undertaking physical mass transfer; they tend to be a carbon-containing compound where the binding agent and method is optimized to create generally balanced and uniform pores and channels to support gas transfer. Such designs result in advective flow of gas molecules such as oxygen in air through a gas diffusion layer to access a layer that catalyzes electron transfer via reduction of an electron acceptor such as the oxygen. By air is intended molecules in a gaseous state such as ambient air or other gaseous molecules containing a species of electron acceptor molecules such as oxygen. A shortcoming of such systems is that such membranes are not waterproof and permit seepage of liquid therethrough. That is, in addition to allowing advective flow of air or oxygen through a porous gas diffusion layer, such structures also permit flow of liquid in the reverse direction, from a cathode catalyst side of the gas diffusion layer towards its air-facing side and "weeping" or leakage of fluid into an air chamber and reduced functionality or failure of the microbial fuel cell.

Efforts to improve the structural integrity of polymeric membranes for use as gas diffusion layers (GDLs) in commercial applications have included the use of carbon fillers such as carbon black, activated carbon, and carbon nanotubes. Increased gas diffusion layer carbon content enhances cathode performance, which has been generally believed to be a function of improved oxygen diffusion due to enhanced material porosity. However, these water-porous materials remain prone to weeping under pressure, a significant drawback.

For microbial fuel cells operating in an aqueous environment it is widely acknowledged that this construct has led to gas diffusion layer weeping under water head pressure, which inhibits performance of such microbial fuel cells, a disadvantageous phenomenon observed throughout the field with regard to conventional microbial fuel cell cathode design. As a result, research has focused trying to balance hydrophobicity of a porous gas diffusion layer that permits advective or bulk flow of air therethrough, while maintaining conductivity. This is a difficult challenge for air breathing electrochemical cells to prevent flooding or weeping from water produced at the cathode and much more difficult for microbial fuel cell that operate within water. Increased pressure imposed on a cathode-side of a gas diffusion layer may force water through pores of a porous gas diffusion layer, even if it has been rendered hydrophobic through inclusion of hydrophobic moieties or other surface treatments, resulting in loss of functionality. The vast majority of literature, which generally does not undertake electrode pressure testing, describes performance increases as carbon content increases, suggesting that the porosity of the carbon provides additional channels for oxygen diffusion, but a result is increased susceptibility to weeping and failure.

Gas diffusion layers may be paired with a catalyst layer to form a cathode. Reduction of oxygen occurs at the cathode layer and a number of materials and techniques can be used to increase surface area or decrease activation losses, each leading to improved performance. Commonly used high surface area materials include activated carbon (AC), AC felt, AC cloth, and/or carbon black. Research has also shown that cathode layers can be treated with reactive compounds such as ammonia and ionomers, to enhance performance. However, increasing the surface area also increases the thickness of the cathode layer and the path length that reduced by-products (e.g. OH—) must travel is also increased. This can lead to a build of reaction by-products that decrease performance.

There is therefore an unmet need for a microbial fuel cell cathode that has sufficient oxygen permeation to permit access of electron-accepting oxygen to a cathode but that can maintain its structural integrity and prevent weeping or flow of fluid through the gas diffusion layer.

SUMMARY OF THE INVENTION

In an aspect, provided are a microbial fuel cell including a cathode and an anode, wherein the cathode includes a waterproof gas diffusion layer which includes a siloxane and a catalyst layer which includes a binder, wherein a surface of the gas diffusion layer opposite the catalyst layer contacts air, and, and the anode includes electrogenic bacteria. In an example, the surface of the gas diffusion layer that contacts air includes a textured surface. IN another example, the binder includes polyvinylidene fluoride, polytetrafluoroethylene, polysulfone, polyphenyl sulfone, polypyrole, poly(p-phenylene vinylene), poly-analine, or tetrafluoroethylene-perfluoro-3,6-dioxa-4-methyl-7-octenesulfonic acid copolymer. In a further example, the catalyst layer includes carbon black, metal shavings, manganese oxide, polypyrole, poly p-phenylenevinylene, poly-analine, tetrafluoroethylene-perfluoro-3,6-dioxa-4-methyl-7-octenesulfonic acid copolymer, an ionomer, or any combination of two or more of the foregoing. In a still further example, the catalyst layer further includes a porous matrix, wherein the matrix includes carbon particles, carbon fibers, carbon threads, activated carbon, carbon black, or any combination of two or more of the foregoing. In an embodiment, the porous matrix includes carbon and is a woven material, a non-woven material, a net, or a screen. In another embodiment, a surface of the gas diffusion layer mates with pores of a surface of the matrix. In an example, the siloxane is poly(dimethylsiloxane) or poly(dimethylsiloxane) in which one or both methyl groups are substituted with a $C_2$-$C_6$ alkyl group. In a particular example, the siloxane is poly(dimethylsiloxane), the surface of the gas diffusion layer that contacts air has a textured surface, the binder includes polyvinylidene fluoride, polytetrafluoroethylene, polysulfone, polyphenyl sulfone, polypyrole, poly(p-phenylene vinylene), poly-analine, or tetrafluoroethylene-perfluoro-3,6-dioxa-4-methyl-7-octenesulfonic acid copolymer, the catalyst layer further includes carbon black, metal shavings, manganese oxide, polypyrole, poly p-phenylenevinylene, poly-analine, tetrafluoroethylene-perfluoro-3,6-dioxa-4-methyl-7-octenesulfonic acid copolymer, an ionomer, or any combination of two or more of the foregoing, and the catalyst layer further includes a porous matrix, wherein the porous matrix includes carbon particles, carbon fibers, carbon threads, activated carbon, carbon black, or any combination of two or more of the foregoing.

In another example, the cathode and the anode are immersed in a liquid. Also provided is a method of generating electricity using a microbial fuel cell as described above, wherein the cathode and the anode are immersed in a liquid and the liquid comprises groundwater, contaminated groundwater, wastewater, sewage, landfill leachate, sugar refinery waste, paper pulping waste, bakery waste, brewery waste, fluid compositions comprising bacterial factors, or any combination thereof.

In another aspect, provided is a method of making a microbial fuel cell, including fabricating a cathode, wherein fabricating includes disposing a siloxane solution onto a surface of a substrate, wherein the siloxane solution includes a siloxane and a solvent, drying the siloxane solution to form a waterproof gas diffusion layer, and placing the gas diffusion layer on a catalyst layer comprising a binder, and facing an anode with the cathode whereby the gas diffusion layer faces away from the anode and contacts air. In an example, the method includes texturing at least one surface of the gas diffusion layer. In an embodiment, texturing includes rolling a textured roller over the gas diffusion layer. Another example includes drying the gas diffusion layer to between 15% by weight solvent and 25% by weight solvent before texturing. A further example includes etching the surface of the gas diffusion layer with plasma. In another embodiment, disposing includes solvent casting, extrusion coating, slot die coating, spraying, or melt casting.

In yet another aspect, provided is a method of making a microbial fuel cell, including fabricating a cathode, wherein fabricating includes disposing a siloxane solution including a siloxane and a solvent onto a catalyst layer including a binder, and drying the siloxane solution to form a waterproof gas diffusion layer, and facing an anode with the cathode whereby the gas diffusion layer faces away from the anode and contacts air. An example includes texturing at least one surface of the gas diffusion layer. In an embodiment texturing includes rolling a textured roller over the gas diffusion layer. Anther embodiment includes drying the gas diffusion layer to between 15% by weight solvent and 25% by weight solvent before texturing. In a further embodiment texturing includes etching the gas diffusion layer with plasma. In another embodiment disposing includes solvent casting, extrusion coating, slot die coating, spraying, or melt casting.

In still a further embodiment the binder includes polyvinylidene fluoride, polytetrafluoroethylene, polysulfone, polyphenyl sulfone, polypyrole, poly(p-phenylene vinylene), poly-analine, or tetrafluoroethylene-perfluoro-3,6-dioxa-4-methyl-7-octenesulfonic acid copolymer. In yet another embodiment the siloxane is poly(dimethylsiloxane) or poly(dimethylsiloxane) in which one or both methyl groups are substituted with a $C_2$-$C_6$ alkyl group. In another embodiment the catalyst layer includes carbon black, metal shavings, manganese oxide, polypyrole, poly p-phenylenevinylene, poly-analine, tetrafluoroethylene-perfluoro-3,6-dioxa-4-methyl-7-octenesulfonic acid copolymer, an ionomer, or any combination of two or more of the foregoing. In a further embodiment disposing includes solvent casting, extrusion coating, slot die coating, spraying, or melt casting. In a further embodiment the catalyst layer further includes a porous matrix and the porous matrix includes carbon particles, carbon fibers, carbon threads, activated carbon, carbon black, or any combination of two or more of the foregoing. In an embodiment, the porous matrix comprises a conductive mesh. In another embodiment the porous matrix includes carbon and is a woven material, a non-woven material, a net, or a screen. In yet another embodiment a surface of the gas diffusion layer mates with pores of a surface of the porous matrix. Still another embodiment includes disposing the siloxane solution onto the porous matrix.

Also provided is a method of making a microbial fuel cell, including fabricating a cathode, wherein fabricating includes disposing a siloxane solution including a siloxane and a solvent onto a first surface of a porous mesh, drying the siloxane solution to form a waterproof gas diffusion layer, and disposing a catalyst layer including a binder on a second surface of the porous mesh, wherein the first surface is opposite to the second surface, and facing an anode with the cathode whereby the gas diffusion layer faces away from the anode and contacts air. In an example, the binder includes polyvinylidene fluoride, polytetrafluoroethylene, polysulfone, polyphenyl sulfone, polypyrole, poly(p-phenylene vinylene), poly-analine, or tetrafluoroethylene-perfluoro-3,6-dioxa-4-methyl-7-octenesulfonic acid copolymer. In another example, the siloxane is poly(dimethylsiloxane) or poly(dimethylsiloxane) in which one or both methyl groups are substituted with a $C_2$-$C_6$ alkyl group. In yet a further example, the catalyst layer includes carbon black, metal shavings, manganese oxide, polypyrole, poly p-phenylenevinylene, poly-analine, tetrafluoroethylene-perfluoro-3,6-dioxa-4-methyl-7-octenesulfonic acid copolymer, an ionomer, or any combination of two or more of the foregoing. In still a further example, the porous matrix includes carbon particles, carbon fibers, carbon threads, activated carbon, carbon black, or any combination of two or more of the foregoing.

In another example, the porous matrix includes a conductive mesh. In a further example, the porous matrix includes carbon and a woven material, a non-woven material, a net, or a screen. In yet another example, a surface of the gas diffusion layer mates with pores of the surface of the porous matrix. In yet a further example, disposing the siloxane solution includes solvent casting, extrusion coating, slot die coating, spraying, or melt casting. In still another example, disposing the catalyst layer includes solvent casting, spray coating, transfer roll processing, extrusion coating, slot die coating, or hot pressing.

Also provided is a method of making a microbial fuel cell, including fabricating a cathode, wherein fabricating includes disposing a siloxane solution comprising a siloxane and a solvent onto a substrate, drying the siloxane solution to form a waterproof gas diffusion layer, and disposing a catalyst layer including a binder on the gas diffusion layer, facing an anode with the cathode whereby the gas diffusion layer faces away from the anode and contacts air. An example includes texturing at least one surface of the gas diffusion layer. In an embodiment, texturing includes rolling a textured roller over the gas diffusion layer. Another embodiment includes drying the gas diffusion layer to between 15% by weight solvent and 25% by weight solvent before texturing. Yet another embodiment includes disposing the catalyst layer before drying the gas diffusion layer to below 25% by weight solvent. In another embodiment, texturing includes etching the gas diffusion layer with plasma.

In another example, disposing the siloxane solution includes solvent casting, extrusion coating, slot die coating, spraying, or melt casting. In a further example, disposing the catalyst layer includes solvent casting, spray coating, transfer roll processing, extrusion coating, or slot die coating. In yet another example, the binder includes polyvinylidene fluoride, polytetrafluoroethylene, polysulfone, polyphenyl sulfone, polypyrole, poly(p-phenylene vinylene), poly-analine, or tetrafluoroethylene-perfluoro-3,6-dioxa-4-methyl-7-octenesulfonic acid copolymer. In yet a further example, the siloxane is poly(dimethylsiloxane) or poly(dimethylsiloxane) in which one or both methyl groups are substituted with a $C_2$-$C_6$ alkyl group. In still another example, the catalyst layer includes carbon black, metal shavings, manganese oxide, polypyrole, poly p-phenylenevinylene, poly-analine, tetrafluoroethylene-perfluoro-3,6-dioxa-4-methyl-7-octenesulfonic acid copolymer, an ionomer, or any combination of two or more of the foregoing. In still a further example, the catalyst layer further includes a porous matrix and the porous matrix comprises carbon particles, carbon fibers, carbon threads, activated carbon, carbon black, or any combination of two or more of the foregoing.

In an embodiment, the porous matrix includes a conductive mesh. In another embodiment, the porous matrix includes carbon and is a woven material, a non-woven material, a net, or a screen. In a further embodiment, a surface of the gas diffusion layer mates with pores of a surface of the porous matrix.

Yet another example further includes immersing the cathode and anode in a liquid. In an embodiment, the liquid includes groundwater, contaminated groundwater, wastewater, sewage, landfill leachate, sugar refinery waste, paper pulping waste, bakery waste, brewery waste, fluid compositions comprising bacterial factors, or any combination thereof.

BRIEF DESCRIPTION OF THE DRAWINGS

These and other features, aspects, and advantages of the present disclosure will become better understood when the following detailed description is read with reference to the accompanying drawings, wherein.

Figure 1:
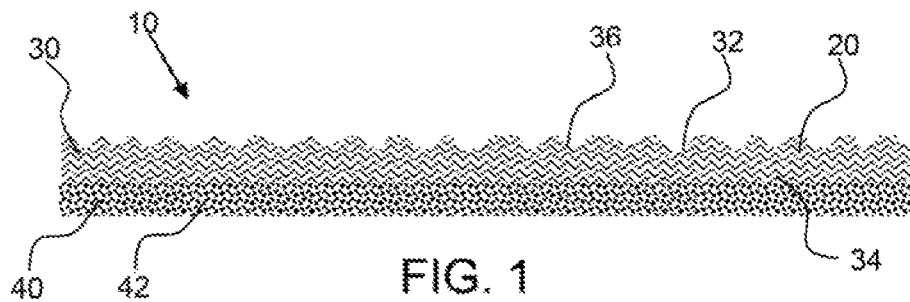
FIG. 1 shows a cross section of an exemplary microbial fuel cell cathode having a gas diffusion layer comprising a siloxane layer having a textured air side surface and a catalyst attached to the cell side of the siloxane layer.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE INVENTION

Disclosed is a microbial fuel cell cathode that has high oxygen permeation rates with no liquid penetration and methods of making and using said cathode and microbial fuel cells including said cathode. An exemplary microbial fuel cell cathode includes a waterproof gas diffusion layer including a siloxane that is non-porous, so that there is no advective or bulk flow of air or liquid through it even under pressure such as when submerged under several feet of water or more or otherwise exposed to elevated water pressure on a cathode side of a GDL. Rather, oxygen or other electron-accepting gas molecules diffuse through the gas diffusion layer. In an exemplary embodiment, the siloxane layer is an integral part of the cathode and includes an air-facing side having a textured surface to increase a surface area of the air side. In some examples, a GDL may merge with a cathode layer or porous mesh at a portion or partial depth of the surface of the GDL that interfaces therewith. In other example, the GDL and cathode catalyst or porous mesh may be adhered to one another without such merging, meting, or interdigitation at a portion of the interface surface therebetween. In all such cases, a GDL is, at least in part, a discrete, nonporous layer that does not permit advective or bulk flow of air or aqueous liquid therethrough.

An increased surface area may reduce mass transfer limitations by providing more area for oxygen molecules to diffuse through the surface of the GDL siloxane to access the catalyst layer of the cathode. An exemplary cathode may include an anode-facing side having a cathode catalyst attached thereto. An exemplary cathode may also include a porous matrix support layer. In some cases a matrix layer may be separate from a catalyst layer and in other cases a catalyst layer may be integrally formed with all or part of a porous mesh. An interface between the GDL siloxane layer and a porous mesh layer may include penetration of a portion of a surface of the GDL layer into a portion of a surface of a layer of a porous matrix. An interface between the cathode catalyst layer and a porous mesh layer may include penetration of a portion of a surface of the cathode catalyst into a portion of a surface of a layer of a porous matrix In an exemplary method of making a microbial fuel cell cathode, a gas diffusion layer mixture including siloxane and organic solvent is solvent cast onto a substrate, coating the substrate or a part of the substrate. The gas diffusion layer mixture may also be disposed on a substrate by extrusion coating, slot die coating, spraying, or melt casting, or by other suitable methods, for example. It may subsequently be dried to form a waterproof gas diffusion layer including a siloxane. An exemplary siloxane is poly(dimethyl siloxane) (PDMS). In other examples, in place of a or both methyl groups of PDMS, the siloxane may include an alkyl (i.e., —$(CH_2)_n$—) group, wherein n is an integer from 2 to 6, or from 2 to 10, or from 2 to 20. In an example, the alkyl group may further be or include an aryl group (e.g., a phenyl group).

The coating process may be done in a continuous manner wherein a roll of substrate material is passed through a coating step from a pay-off roll and may subsequently be dried and taken up on a take-up roll. In another embodiment, the coated substrate is cut into sheets after coating with the gas diffusion layer mixture and/or after a drying step. Drying may be by exposure to ambient air for a period of time, with or without induced air flow to decrease drying time, and/or exposure to elevated temperature to decrease drying time. In some examples, drying (of a GDL or cathode catalyst layer) may also include drying in an oven including exposure to elevated temperatures such as at 90° C. or higher, or at 100° C. or higher, or 110° C. or higher, for one, two, three, four, five, six, seven, eight, nine, ten, eleven, or twelve hours, or longer, or at temperatures or durations therebetween.

A cathode catalyst may possess three general properties. It may by capable of catalyzing reduction of oxygen molecules whereby electrons, produced by electrogenic microbes on an anode of a microbial fuel cell, are accepted by oxygen. A catalyst may also be electrically conductive so that electrons may flow through it. And a catalyst may have high surface area to increase the amount of electron transfer to oxygen molecules that may be catalyzed. Carbon-containing constituents are useful for such purposes (e.g., activated carbon, carbon black, etc.). Optionally, a catalyst layer may also include other constituents such as metal shavings, an ionomer or ionomers (e.g., NAFION (i.e. tetrafluoroethylene-perfluoro-3,6-dioxa-4-methyl-7-octenesulfonic acid copolymer), FUMASEP or FUMAPEM (Fumatech GbH), CMI-7001, AMI-7001 (Membranes International, Inc), or AS-4 (Tokuyama)), poly-aniline, manganese oxide, polypyrole, poly p-phenylenevinylene, a siloxane such as PDMS, or any two or more of the foregoing in any combination. Such constituents or additives may increase surface area, conductivity, or catalytic ability of a catalyst layer to improve electron and thus current flow and, ultimately, generation of electricity.

A cathode catalyst layer may further be in contact with a more highly conductive material such as various metals with higher conductive capacity to facilitate and expedite electron transfer through a circuit including the cathode catalyst.

A catalyst layer may also include a binder, to hold constituents of a catalyst layer together to form a discrete layer and/or to increase adhesion to an adjacent layer such as a GDL or porous mesh. A binder may include polyvinylidene fluoride, polytetrafluoroethylene, polysulfone, polyphenyl sulfone, polypyrole, poly(p-phenylene vinylene), poly-analine, or tetrafluoroethylene-perfluoro-3, 6-dioxa-4-methyl-7-octenesulfonic acid copolymer. A binder may also include a siloxane such as PDMS or other siloxane. A catalyst layer may be formed by combining various combinations of the foregoing together in an appropriate solvent (e.g., N-methyl-2-pyrrolidone or other solvent as may be suitable for a binder and/or other constituents of a catalyst layer) then disposing them onto a surface or a GDL or a porous matrix as disclosed and drying it, such as by air drying or heating such as in an oven. Catalyst layer may be removed from a substrate on which it is formed then attached or adhered to a GLD or a porous mesh or a surface onto which it is disposed and formed may become part of the cathode.

A catalyst is combined with the gas diffusion layer to form a cathode that has substantially no bulk flow of air or liquid therethrough, as described herein. In use, one surface of the GDL faces air or other source of gaseous oxygen and the other surface of the GDL faces a cathode catalyst layer (with or without or including or not including a porous mesh), which cathode catalyst layer in turn faces an anode via its non-GDL-facing surface. The gas diffusion layer or siloxane layer may be texturized to increase the specific surface area, or area per unit area of the gas diffusion layer. The gas diffusion layer may be texturized on one or both sides. Textured includes pocked, lined, etched, scalloped, roughed, or otherwise scored, scratched, notched, or rendered bumpy, stochastically or in a patterned manner, to increase surface area.

In an exemplary embodiment, the gas diffusion layer is texturized by contact with a formed or texturized roller after the gas diffusion layer mixture is coated onto the substrate. Again, this may be done in a continuous manner, wherein the substrate is coated with the gas diffusion layer mixture and then fed to contact the formed roller in a continuous manner. The gas diffusion layer mixture may be partially dried or substantially dried, such as having no more than about 20% by weight solvent before contacting the formed roller, or between 15% and 25% weight solvent, or between 10% weight and 15% weight solvent, or between 15% and 20% weight solvent, or between 20% weight and 25% weight solvent, or less than 10% weight but more than 1% weight solvent. Another exemplary texturing method includes exposure to plasma, wherein chemical bonds are broken by exposure to the plasma to create voids in the surface.

The substrate may itself include or be a catalyst layer thereby forming a cathode upon drying of the gas diffusion layer mixture disposed on said substrate. In another exemplary method, a catalyst layer may be applied to the gas diffusion layer or the gas diffusion layer mixture disposed on the substrate. The catalyst may be applied to the gas diffusion layer mixture before it is completely dried (i.e., having no more than about 20% by weight solvent before contacting the formed roller, or between 15% and 25% weight solvent, or between 10% weight and 15% weight solvent, or between 15% and 20% weight solvent, or between 20% weight and 25% weight solvent, or less than 10% weight but more than 1% weight solvent), wherein the gas diffusion layer mixture may act as a binding agent to affix the catalyst to the gas diffusion layer. The catalyst layer may be applied through a spray coating, a transfer roll process, including a gravure roll coating, wherein the transfer roller has a surface texture to pick up the catalyst that is then deposited onto the gas diffusion layer mixture, or gas diffusion layer. The catalyst layer may be disposed by solvent casting, spray coating, transfer roll processing, extrusion coating, slot die coating, or hot pressing, as non-limiting examples. The catalyst may be combined with a solvent or carrier for coating onto the gas diffusion layer.

An exemplary substrate is non-porous, such as film of material, including but not limited to fluoropolymer film or polyimide film. When manufacture of a cathode includes separation of a catalyst or GDL layer from a substrate on which it was formed, a preferred substrate film has good release properties, a low surface tension, is solvent tolerant, absorbs little solvent, and is thermally stable at high temperatures, for drying a siloxane solution in an oven to form a GDL for example. In an exemplary embodiment, a gas diffusion layer mixture is coated onto a high temperature film, and a catalyst layer is attached before drying. The dried cathode (including GDL and catalyst layer) can then be removed from the carrier film.

Another exemplary substrate may be porous or a porous matrix layer which may form part of the cathode. A porous matrix layer may comprise catalyst which may be on one or both sides or throughout the thickness of the porous matrix layer. An exemplary porous matrix layer has pores or a porous network that extend through the thickness, wherein the porous matrix layer is gas permeable allowing a flow of air or liquid through the thickness of the material. In addition, an exemplary porous matrix layer is electrically conductive and may comprise conductive particles, conductive fibers, wire, and the like. An exemplary porous matrix layer may comprise carbon, such as carbon particles, carbon black, carbon fibers or threads and the like. For example a porous matric may include carbonized steel mesh, or other conductive mesh. A cathode catalyst may be configured with the carbon. For example, a catalyst layer may be formed by being disposed on a porous mesh and thereby infuse or mate with the pores on the surface of the porous mesh such that the a portion of the surface of the porous mesh may become interdigitated or mated with and become part of the catalyst layer as the catalyst layer dries after being disposed. In other examples a porous mesh may be adhered to a surface of a catalyst layer without such mating or interdigitating.

Similarly, a GDL may be formed on a porous mesh such that an interface of a surface of the GDL with the porous mesh interdigitates or mates with the porous mesh. For example the GDL siloxane solution me be disposed on a porous mesh such that, upon drying to form the GDL, there is overlap between a surface of the GDL that interfaces with the porous mesh and the surface of the porous mesh that interfaces with the GDL. In other examples, a porous mesh may be adhered to a surface of a GDL without such mating or interdigitating.

Carbon of a porous mesh or catalyst layer or both may be activated carbon or carbon black, for example. It may be a woven carbon material or a carbon fabric, or fibrous carbon. An exemplary porous matrix layer may be a conductive mesh having openings that extend directly through the thickness of the material. An exemplary porous matrix layer may be a woven or non-woven material or fabric, a net or screen. In an exemplary embodiment, the porous matrix layer is a woven conductive fabric comprising carbon yarns or threads.

A cathode having a siloxane layer, as described herein, and minimal carbon, provides for selective transfer of oxygen by siloxane layer via diffusion (rather than advection) of gaseous oxygen through the waterproof nonporous siloxane-containing GDL. Thus, air on one side of the GDL is separated from liquid on the other, cathode-facing side of the GDL. The concentration by weight of siloxane in the gas diffusion layer may be about 50% or more, about 75% or more, about 90 or 95% or more and any range between and including the concentrations provided. A discrete, non-porous, waterproof siloxane-containing GDL is a fundamentally different architecture for oxygen transport than traditional microbial fuel cells, which conventionally use gas diffusion layers that are not fully waterproof in that they are porous and do not include a discrete siloxane-containing GDL, relying on oxygen transfer via advection rather than diffusion, leaving the GDL susceptible to weeping under pressure. Conventionally, when subjected to elevated pressure, such porous GDLs fail because elevated pressure causes weeping of liquid through pores, whereas failure of a discrete, waterproof GDL under pressure as disclosed herein would occur, if at all, from bursting or rupture of the GDL rather than weeping of liquid through the pores.

A discrete, waterproof, siloxane-containing GDL as disclosed herein thus allows for efficient microbial fuel cell performance at higher pressure than the upper limit of pressure permitted for functioning of conventional microbial fuel cells with liquid-permeable gas diffusion layers. Although such porous GDL's which allow air or liquid to pass through in bulk have in some previous examples been surface-treated with hydrophobic compounds to repel liquid to maintain integrity of the liquid-air boundary, ultimately under even relatively low levels of pressure the force of liquid overcomes repulsion of hydrophobic treatment and liquid weeps through the GDL leading to failure of the microbial fuel cell. As disclosed herein, a microbial fuel cell with a discrete, non-porous, waterproof GDL containing siloxane overcomes such problems and prevents weeping under pressure.

The GDL siloxane resists water flux therethrough, wherein there is no bulk flow of water through the GDL siloxane layer. Therefore, a cathode resists water head pressure while maintaining consistent oxygen transfer via diffusion of oxygen from the air side of the GDL to the cathode side and microbial fuel cell performance. The methods of making the cathode, as described herein, can be continuous and scalable for high volume requirements. A cathodes made by these novel methods may be non-weeping wherein they are resistant to water head pressure, an important performance requirement when operating under water, at depths of several inches, a foot, several feet, 10 or more feet, 20 or more feet, 50 or more feet, or deeper. Exemplary cathodes therefore prevent the weeping failure mode exhibited by conventional, permeable cathodes.

An exemplary gas diffusion layer, as described in any of the embodiment herein, may have a thickness of about 25 um or more, about 50 um or more, about 75 um or more, about 100 um or more and any range between and including the thicknesses provided. The thinner the gas diffusion layer the less resistance to oxygen permeation therethrough, whereas a thicker GDL may be burst-resistant to higher levels of water pressure. A support layer may be configured on one or both sides of the gas diffusion layer to increase bursting resistance. For example, a supportive screen, bracing, matrix, mesh, or other supportive reinforcement, that allows oxygen pass-through so as to access GDL surface, may further support a GDL so that it is less likely to burst r rupture under pressure. Such reinforcement would be ineffective for conventional GLDs that are porous or otherwise liquid permeable because liquid would weep or seep through in portions not directly supported by the reinforcing support (e.g., at openings in the screen, mesh, bracing, etc, where oxygen access to the GDL is allowed). In some examples, a porous mesh as described above may also provide structural support for a GDL as described herein.

An exemplary catalyst layer, as described in any of the embodiment herein, may have a thickness of about 200 um or more, about 250 um or more, about 300 um or more and any range between and including the thicknesses provided.

A cathode may face an anode, wherein the anode includes electrogenic microbes. A catalyst side of the cathode may face the anode (being on the cell-side of the GDL). The cell side, including the cathode and anode, may be immersed in liquid, such as a liquid containing a carbohydrate or other nutrient source for catabolism by the microbes of the anode. For example the liquid may be groundwater, contaminated groundwater, wastewater, sewage, landfill leachate, sugar refinery waste, paper pulping waste, bakery waste, brewery waste, fluid compositions comprising bacterial factors, or any combination thereof. As microbes catabolize the nutrients of the liquid generating a potential, the cathode catalyzes transfer of electrons to an ultimate electron acceptor such as oxygen, accessing the catalyst layer by diffusing from the air-side of the GDL (i.e., the surface of the GDL opposite to the cell-side or catalyst-facing surface or anode-facing surface). This flow of electrons creates an electric current, transferred for example out of the cell and used to charge a battery, power a connected device, etc. In some examples inclusion of a conductive porous mesh in or addition of a conductive porous mesh to a catalyst layer or cathode may increase electron flow and thereby increase electricity generation by a microbial fuel cell, thereby collecting the current generated, as described. In some examples a porous mesh may be manufactured and configured so as to collect current in this manner.

The summary of the invention is provided as a general introduction to some of the embodiments of the invention, and is not intended to be limiting. Additional example embodiments including variations and alternative configurations of the invention are provided herein.

EXAMPLES

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

The size and proportions are not to scale. For all of the following descriptions of examples, examples described are non-limiting examples. Claims are not to be limited to any one of the following examples, which are offered as selections of embodiments all of which, and many others, are included within the present disclosure through combinations of features as disclosed.

As shown in FIG. 1, an exemplary microbial fuel cell cathode 10 has a gas diffusion layer 20 comprising a siloxane layer 30 having a textured surface 36 on the air side 32 and a catalyst 40 attached to the anode-facing (i.e., cell) side 34 of the siloxane layer. The catalyst may be a catalyst on a conductive particle, such as a carbon, or activated carbon particle.

Figure 2:
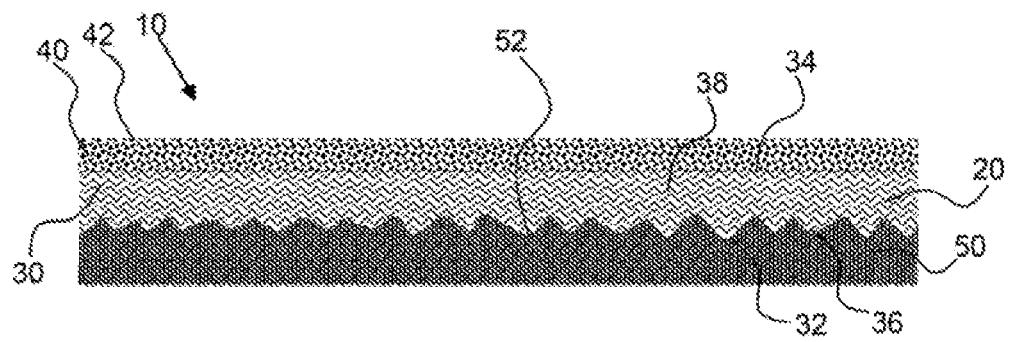
FIG. 2 shows a cross section of an exemplary microbial fuel cell cathode on a texturized substrate.

As shown in FIG. 2, an exemplary microbial fuel cell cathode 10 is formed on a substrate 50 having a texturized surface 52. The siloxane solution 38 is cast on the substrate to form the siloxane layer 30 and the catalyst 40 is attached to the siloxane layer. The siloxane solution may be dried to form the siloxane layer by active heating or by ambient air drying and the catalyst may be attached to the siloxane layer prior to the complete drying and/or curing of the siloxane layer to provide adequate adhesion.

Figure 3:
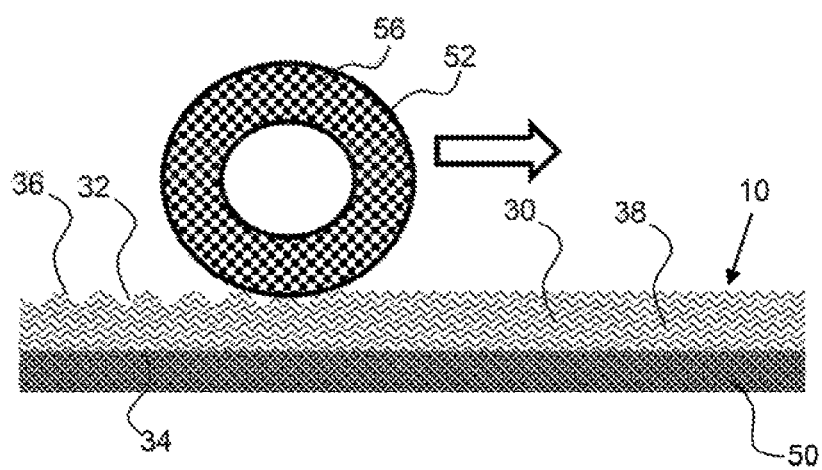
FIG. 3 shows a cross section of an exemplary gas diffusion layer being formed by a roller having a texturizing surface.

As shown in FIG. 3, an exemplary gas diffusion layer 20 is being formed by a roller 56 having a texturizing surface 52 rolling over a cast siloxane solution 38 on a substrate 50. The roller may be rolled over the siloxane solution when it is partially dried or cured to enable the roller to produce a permanent texturized surface 36 in the siloxane layer 30.

Figure 4:
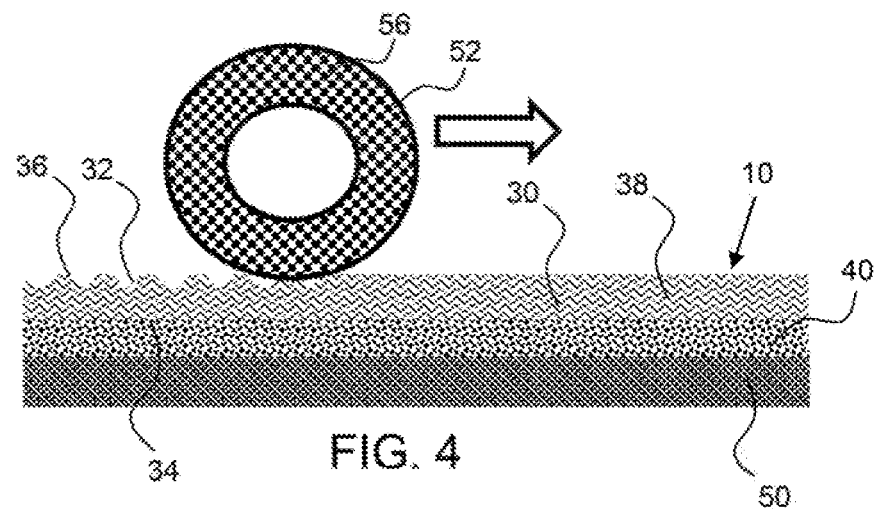
FIG. 4 shows a cross section of an exemplary microbial fuel cell cathode with a roller having a texturizing surface producing a textured surface on the gas diffusion layer.

As shown in FIG. 4, an exemplary gas diffusion layer 20 is being formed by a roller 56 having a texturizing surface 52 rolling over a cast siloxane solution 38 on a substrate 50 having a catalyst 40 thereon. Again, the roller may be rolled over the siloxane solution when it is partially dried or cured to enable the roller to produce a permanent texturized surface 36 in the siloxane layer 30.

Figure 5:
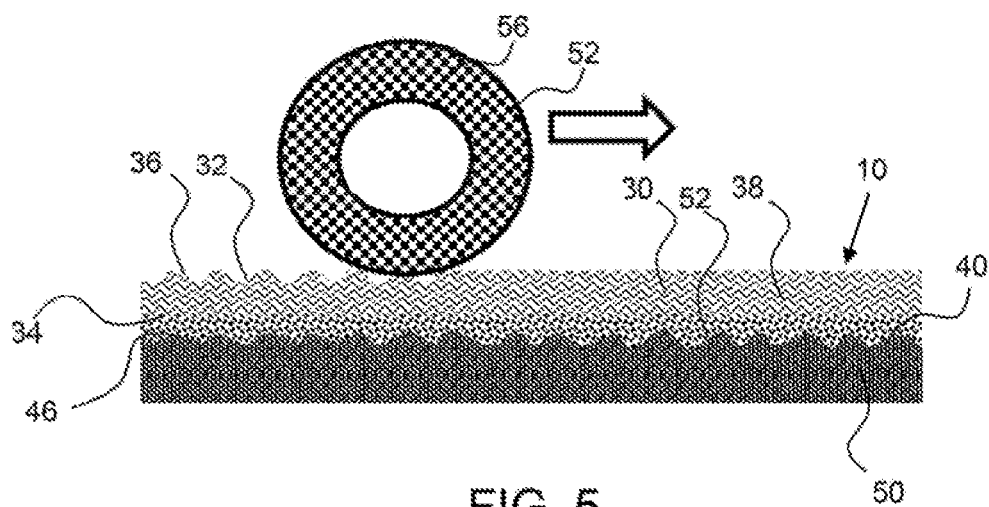
FIG. 5 shows a cross section of an exemplary microbial fuel cell cathode with a roller having a texturizing surface producing a textured surface on the gas diffusion layer and a texturized substrate having a catalyst layer thereon.

As shown in FIG. 5, an exemplary gas diffusion layer 20 is being formed by a roller 56 having a texturizing surface 52 rolling over a cast siloxane solution 38 on a substrate 50 having a catalyst 40 thereon. The substrate 50 has a texturizing surface 52 that increases the surface area of the catalyst layer 40 by producing a texturized surface 46 in the catalyst layer.

Figure 6:
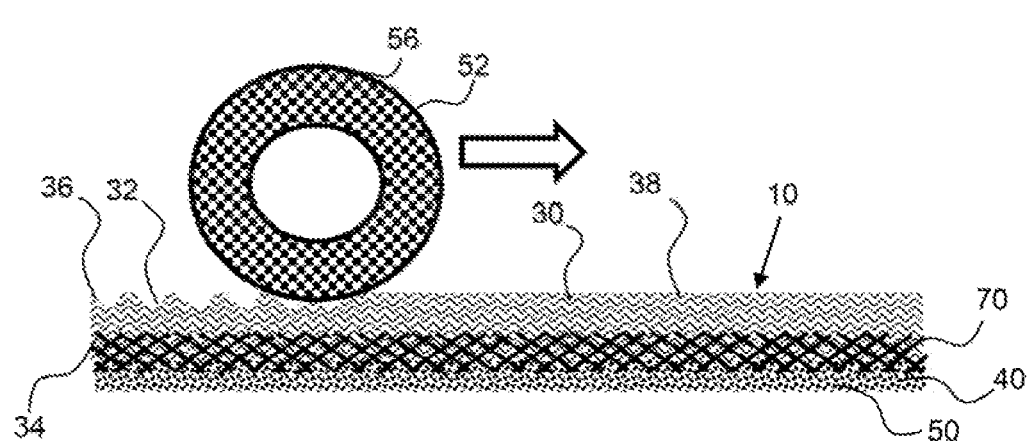
FIG. 6 shows a cross section of an exemplary microbial fuel cell cathode with a roller having a texturizing surface producing a textured surface on the gas diffusion layer and a catalyst and porous matrix support layer on the substrate.

As shown in FIG. 6, an exemplary gas diffusion layer 20 is being formed by a roller 56 having a texturizing surface 52 rolling over a cast siloxane solution 38 on a substrate 50 comprising a porous matrix support layer 70 and catalyst 40 thereon. The porous matrix support layer 70 and catalyst 40 may be combined with each other prior to placement on the substrate 50. The porous matrix support layer 70 and catalyst 40 acts as a substrate for casting the siloxane solution 38 thereon. The porous matrix support layer may be a woven conductive fabric, a non-woven conductive fabric, or a sintered conductive material.

Figure 7:
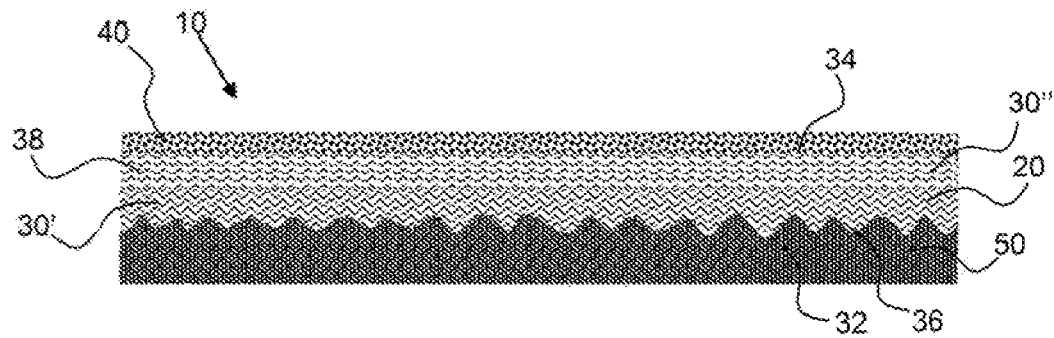
FIG. 7 shows a cross section of an exemplary microbial fuel cell cathode on a texturized substrate having a siloxane layer thereon, and a siloxane solution cast on the first siloxane layer and a catalyst on the second siloxane solution layer.

As shown in FIG. 7, an exemplary microbial fuel cell cathode 10 is cast on a substrate 50 having a texturizing surface 52. The first siloxane layer 30' may be a thin film, or may be siloxane solution that is substantially dried before application of the siloxane solution 38. The siloxane solution has solvent that enables the adhesion of the second siloxane layer 30" when the siloxane solution dries and cures. A catalyst 40 may be applied to the siloxane solution before it is completely dried and cured.

Figure 8:
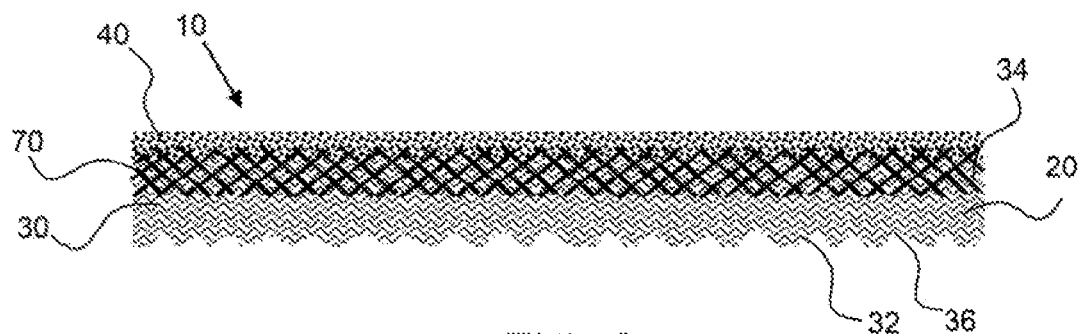
FIG. 8 and FIG. 9 show a cross section of an exemplary microbial fuel cell cathode that has been removed from a texturized substrate having a siloxane layer, a porous matrix support layer and a catalyst.
Figure 9:
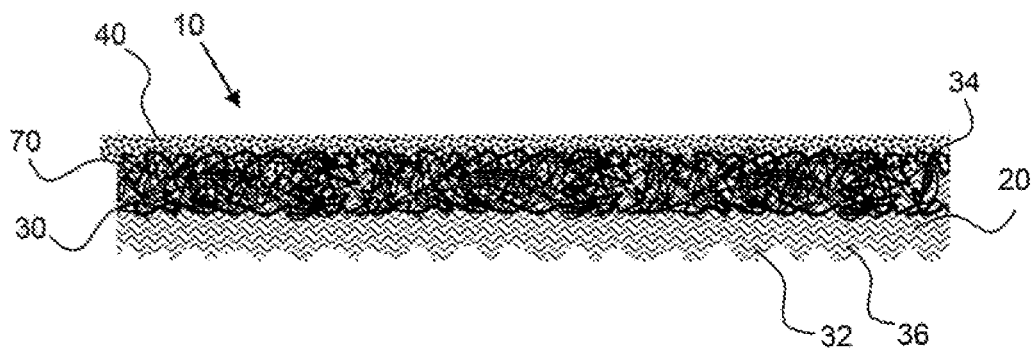

As shown in FIGS. 8 and 9, an exemplary microbial fuel cell cathode 10 has been removed from a texturized substrate and has a siloxane layer 30, a porous matrix support layer 70 and a catalyst 40. The porous matrix support layer is on the cell side 34 of the siloxane layer 30. The air side 32 of the siloxane layer has a textured surface 36 to increase surface area to increase oxygen permeation therethrough.

Figure 10:
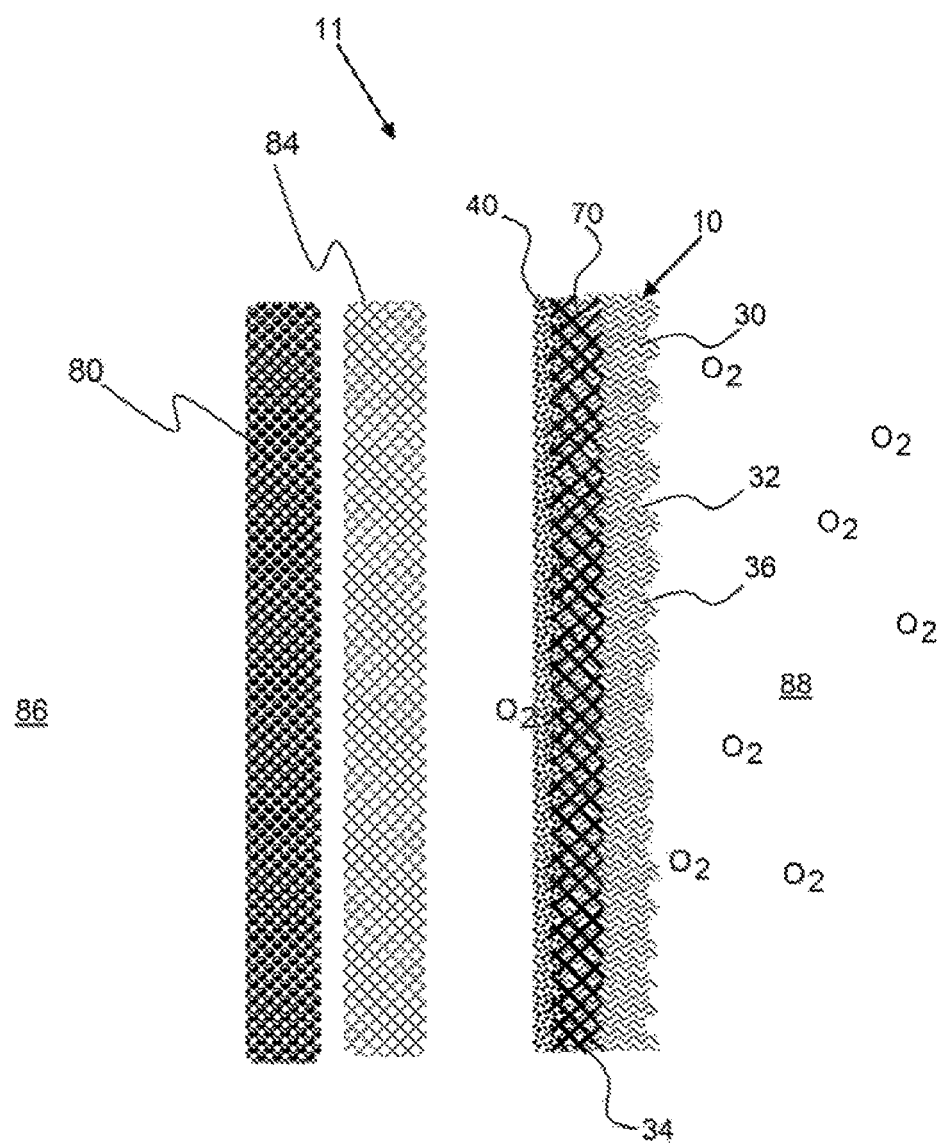
FIG. 10 shows a diagram of a microbial fuel cell having an exemplary microbial fuel cell cathode having a texturized air side.

As shown in FIG. 10, a microbial fuel cell 11 has an exemplary microbial fuel cell cathode 10 having a siloxane layer 30 with a texturized surface 36 on the air side 32 of the siloxane layer. The microbial fuel cell has an air side 88 and a liquid side 86. The microbial fuel cell cathode interfaces with the air side and the catalyst 40 faces the anode 80. A spacer 84 that is permeable to liquid may be configured between the anode 80 and the cathode 10. A porous matrix support layer 70 may act as the current collector for the cathode. Oxygen may permeate through the siloxane layer to the catalyst 40 to enable the chemical reactions to produce electrical current.

Some examples disclosed herein include methods of making a microbial fuel cell. Also included are methods of making a cathode component of a microbial fuel cell. In some examples, aspects or features of the present disclosure are present upon fabricating a cathode for a microbial fuel cell without or before subsequent inclusion of the cathode in a microbial fuel cell. In other examples, a microbial fuel cell may be made as disclosed, with or without or before or after immersing a cathode or anode in water or other liquid, or using a microbial fuel cell in generating electricity.

It would be understood that all permutations of the foregoing features are included within the present disclosure even if an individual combination of features was not explicitly recited. For example, all combinations of all binders with or without all described additives to a catalyst layer are explicitly included as intended examples of the present disclosure. Furthermore, all disclosed examples of siloxanes for a GDL are explicitly included within the present disclosure, as are all possible examples of any and all such siloxanes in combination with any and all catalyst layers including any of the aforementioned binders with or without any of the aforementioned additional additives to a gas diffusion layer, in all possible combinations and permutations.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A microbial fuel cell comprising
a cathode, an anode, and a current collector for the cathode, wherein
the cathode comprises a discrete waterproof, nonporous gas diffusion layer and a catalyst layer, and the catalyst layer comprises a cathode current collector, wherein the cathode current collector is a porous matrix, the waterproof gas diffusion layer comprises a siloxane and a surface that contacts air, wherein the surface that contacts air is opposite the catalyst layer, the catalyst layer comprises a binder, and the anode comprises electrogenic bacteria.

2. The microbial fuel cell of claim 1, wherein the surface of the gas diffusion layer that contacts air comprises a textured surface.

3. The microbial fuel cell of claim 1, wherein the binder comprises polyvinylidene fluoride, polytetrafluoroethylene, polysulfone, polyphenyl sulfone, polypyrole, poly(p-phenylene vinylene), poly-analine, or tetrafluoroethylene-perfluoro-3,6-dioxa-4-methyl-7-octenesulfonic acid copolymer.

4. The microbial fuel cell of claim 1, wherein the catalyst layer comprises carbon black, metal shavings, manganese oxide, polypyrole, poly p-phenylenevinylene, poly-analine, tetrafluoroethylene-perfluoro-3,6-dioxa-4-methyl-7-octenesulfonic acid copolymer, an ionomer, or any combination of two or more of the foregoing.

5. The microbial fuel cell of claim 1, wherein the porous matrix comprises carbon particles, carbon fibers, carbon threads, activated carbon, carbon black, or any combination of two or more of the foregoing.

6. The microbial fuel cell of claim 5, wherein the porous matrix comprises carbon and is a woven material, a nonwoven material, a net, or a screen.

7. The microbial fuel cell of claims 5 wherein a surface of the gas diffusion layer mates with pores of a surface of the porous matrix.

8. The microbial fuel cell of claim 1 wherein the siloxane is poly(dimethylsiloxane) or poly(dimethylsiloxane) in which one or both methyl groups are substituted with a $C_2$-$C_6$ alkyl group.

9. The microbial fuel cell of claim 1, wherein
the siloxane comprises poly(dimethylsiloxane),
the surface of the gas diffusion layer that contacts air comprises a textured surface,
the binder comprises polyvinylidene fluoride, polytetrafluoroethylene, polysulfone, polyphenyl sulfone, polypyrole, poly(p-phenylene vinylene), poly-analine, or tetrafluoroethylene-perfluoro-3,6-dioxa-4-methyl-7-octenesulfonic acid copolymer,
the catalyst layer further comprises carbon black, metal shavings, manganese oxide, polypyrole, poly p-phenylenevinylene, poly-analine, tetrafluoroethylene-perfluoro-3,6-dioxa-4-methyl-7-octenesulfonic acid copolymer, an ionomer, or any combination of two or more of the foregoing,
and the porous matrix comprises carbon particles, carbon fibers, carbon threads, activated carbon, carbon black, or any combination of two or more of the foregoing.

10. The microbial fuel cell of claim 1, wherein the cathode and the anode are immersed in a liquid.

11. A method of making a microbial fuel cell, comprising fabricating a cathode, wherein fabricating comprises
disposing a siloxane solution onto a surface of a substrate, wherein the siloxane solution comprises a siloxane and a solvent,
drying the siloxane solution to form a discrete waterproof, nonporous gas diffusion layer, and
placing the gas diffusion layer on a catalyst layer comprising a binder to form the cathode, wherein the catalyst layer further comprises a cathode current collector and the cathode current collector is a porous matrix, and facing an anode with the cathode whereby the gas diffusion layer faces away from the anode and contacts air.

12. The method of claim 11, comprising texturing at least one surface of the gas diffusion layer.

13. The method of claim 12, wherein texturing comprises rolling a textured roller over the gas diffusion layer.

14. The method of claim 12, comprising drying the gas diffusion layer to between 15% by weight solvent and 25% by weight solvent before texturing.

15. The method of claim 12, wherein the surface of the substrate is textured.

16. The method of claim 11, wherein texturing comprises etching the gas diffusion layer with plasma.

17. The method of claim 11, wherein disposing comprises solvent casting, extrusion coating, slot die coating, spraying, or melt casting.

* * * * *